United States Patent
Kalafatis et al.

(10) Patent No.: US 11,360,077 B2
(45) Date of Patent: Jun. 14, 2022

(54) DEATH RECEPTORS AS MARKERS FOR RHTRAIL-SENSITIVITY

(71) Applicant: Cleveland State University, Cleveland, OH (US)

(72) Inventors: Michael Kalafatis, Shaker Heights, OH (US); Katherine Turner, Chardon, OH (US)

(73) Assignee: Cleveland State University, Cleveland, OH (US)

( * ) Notice: Subject to any disclaimer, the term of this patent is extended or adjusted under 35 U.S.C. 154(b) by 106 days.

(21) Appl. No.: 15/918,635

(22) Filed: Mar. 12, 2018

(65) Prior Publication Data

US 2018/0348202 A1     Dec. 6, 2018

Related U.S. Application Data

(60) Provisional application No. 62/469,879, filed on Mar. 10, 2017.

(51) Int. Cl.
| | | |
|---|---|---|
| *G01N 33/50* | (2006.01) | |
| *G01N 33/574* | (2006.01) | |
| *G01N 15/14* | (2006.01) | |
| *A61K 31/352* | (2006.01) | |
| *A61P 35/00* | (2006.01) | |
| *G01N 15/10* | (2006.01) | |

(52) U.S. Cl.
CPC ......... *G01N 33/5008* (2013.01); *G01N 15/14* (2013.01); *G01N 15/1459* (2013.01); *G01N 33/574* (2013.01); *G01N 33/5743* (2013.01); *A61K 31/352* (2013.01); *A61P 35/00* (2018.01); *G01N 2015/1006* (2013.01); *G01N 2015/1477* (2013.01); *G01N 2015/1488* (2013.01); *G01N 2500/10* (2013.01); *G01N 2800/52* (2013.01)

(58) Field of Classification Search
CPC ............... G01N 33/5008; G01N 15/14; G01N 15/1459; G01N 33/574; G01N 33/5743; G01N 2015/1006; G01N 2015/1477; G01N 2015/1488; G01N 2500/10; G01N 2800/52; A61P 35/00; A61K 31/352
USPC ........................................................... 435/29
See application file for complete search history.

(56) References Cited

U.S. PATENT DOCUMENTS

2010/0210545 A1* 8/2010 Araki ................... C12Q 1/6886
                                                                514/1.1

OTHER PUBLICATIONS

Yoshida et al., Repeated Treatment with Subtoxic Doses of TRAIL Induces Resistance to Apoptosis through Its Death Receptors in MDA-MB-231 Breast Cancer Cells, Molecular Cancer Research, vol. 7, No. 11, (2009), pp. 1835-1844.*
Spierings et al., Expression of TRAIL and TRAIL Death Receptors in Stage III Non-Small Cell Lung Cancer Tumors, Clinical Cancer Research, vol. 9, (2003), pp. 3397-3405.*
Van Geelen et al., Modulation of TRAIL resistance in colon carcinoma cells: Different contributions of DR4 and DR5, BMC Cancer, vol. 11, (2011), pp. 1-13.*
Psahoulia et al., Quercetin enhances TRAIL-mediated apoptosis in colon cancer cells by inducing the accumulation of death receptors in lipid rafts, Molecular Cancer Therapeutics, vol. 6, No. 9, (2007), pp. 2591-2599.*

* cited by examiner

*Primary Examiner* — Jennifer M. H. Tichy
(74) *Attorney, Agent, or Firm* — Calfee, Halter & Griswold, LLP

(57) ABSTRACT

Disclosed are methods and compositions for identifying and treating certain conditions and diseases. In certain instances, the general inventive concepts provide methods for determining rhTRAIL sensitivity of a sample and/or methods and compositions for inducing apoptosis to treat conditions and diseases with rhTRAIL.

12 Claims, 15 Drawing Sheets

Specification includes a Sequence Listing.

DEATH RECEPTORS AS MARKERS FOR RHTRAIL-SENSITIVITY

CROSS-REFERENCE TO RELATED APPLICATIONS

This application claims the benefit of U.S. Provisional Patent Application No. 62/469,879, filed Mar. 10, 2017, the content of which is hereby incorporated by reference in its entirety.

FIELD

The general inventive concepts relate to cancer therapy, and more particularly, to the field of personalized therapies for cancer treatment.

BACKGROUND

There is an ever-evolving need to develop new and more effective cancer treatments. Malignant melanoma is the most commonly-diagnosed skin cancer and is associated with a high rate of metastasis. The frequency of malignant melanoma has been on the rise over the last 30 years. Although it is the least diagnosed of the skin cancers, it is associated with the highest rate of mortality. When the melanoma is localized to the epidermis, the survival rate is 98%. However, once the cancer metastasizes the 5 year survival rate decreases to 17%. Current therapies (chemotherapy, radiation therapy, targeted therapy and immunotherapy) are characterized by slow efficacy and only temporary anti-tumor properties due to acquired resistance. In addition, a high degree of negative side effects are associated with these therapies which deeply impacts the patient's quality of life and limits the optimum drug dose. As a result, there is no standard therapeutic regimen for metastatic malignant melanoma. Accordingly, there is a need for the development of therapies that effectively treat the disease while avoiding many of the common drawbacks or side effects of current therapies. Low stage melanoma is easily treated, but metastatic malignant melanoma is an extremely treatment-resistant malignancy with low survival rates.

Accordingly, there is an unmet need for solutions that are effective to treat one or more of the conditions or diseases described herein, including but not limited to new efficient and non-toxic treatment of cancers, including malignant melanoma.

SUMMARY

The general inventive concepts relate to and contemplate compositions and methods for treating conditions and diseases via induction of apoptosis.

Recombinant human Tumor Necrosis Factor-Related Apoptosis-Inducing Ligand (rhTRAIL) holds great promise as a cancer therapy due to its selectivity for cancer cells. The application of rhTRAIL for the treatment of metastatic malignant melanoma holds considerable promise due to its selective pro-apoptotic activity towards cancer cells and not non-transformed cells.

In certain exemplary embodiments, the general inventive concepts relate to a pharmaceutical composition useful for ameliorating and/or treating cancer, including malignant melanoma. The composition may comprise an effective amount of rhTRAIL and, in certain instances, an effective amount of a polyphenol that increases the sensitivity of one or more cells to rhTRAIL. One such polyphenol is quercetin.

In certain exemplary embodiments, the general inventive concepts relate to a method of ameliorating and/or treating cancer, including malignant melanoma. The method comprises administering, to an individual in need thereof, a composition comprising an effective amount of rhTRAIL and, in certain instances, an effective amount of a polyphenol that increases the sensitivity of one or more cells to rhTRAIL.

In certain exemplary embodiments, the general inventive concepts relate to a method of increasing the rhTRAIL sensitivity of one or more target cells. The method comprises identifying one or more cells having a low or reduced rhTRAIL sensitivity (i.e., the cells or tissue is not rhTRAIL sensitive) and administering an effective amount of a polyphenol that increases the sensitivity of one or more cells to rhTRAIL until the desired rhTRAIL sensitivity is achieved. One such polyphenol is quercetin.

In certain exemplary embodiments, the general inventive concepts contemplate an in vitro test to analyze tumor cells isolated from patients for the membrane expression of death receptors (DRs) to determine their suitability for rhTRAIL-treatment (i.e., rhTRAIL sensitivity). Surprisingly, a correlation between DR membrane expression (in particular, DR4 and DR5) and rhTRAIL-sensitivity has been discovered. The membrane expression of DR4 and DR5 was examined through staining with anti-DR4 and DR5 followed by FACS. rhTRAIL-sensitivity was determined through Annexin-V and PI staining and western blotting post rhTRAIL-treatment.

The general inventive concepts are based, in large part, on the dual discoveries that rhTRAIL sensitivity can be rapidly and reproducibly characterized, and that rhTRAIL-resistance can be abrogated through the administration of particular naturally-derived polyphenols (i.e., quercetin). Treatment with quercetin can modulate cellular components responsible for rhTRAIL-resistance. Thus, rhTRAIL-resistant malignant melanomas are sensitized by quercetin. Quercetins action is manifested by the upregulation of rhTRAIL-binding receptors DR4 and DR5 on the surface of cancer cells and by an increase of the proteasome-mediated degradation of the anti-apoptotic protein FLIP. Thereby, cells are more susceptible to apoptosis when exposed to rhTRAIL.

BRIEF DESCRIPTION OF THE DRAWINGS

The general inventive concepts, as well as embodiments and advantages thereof, are described below in greater detail, by way of example, with reference to the drawings in which.

DETAILED DESCRIPTION

Figure 1A:
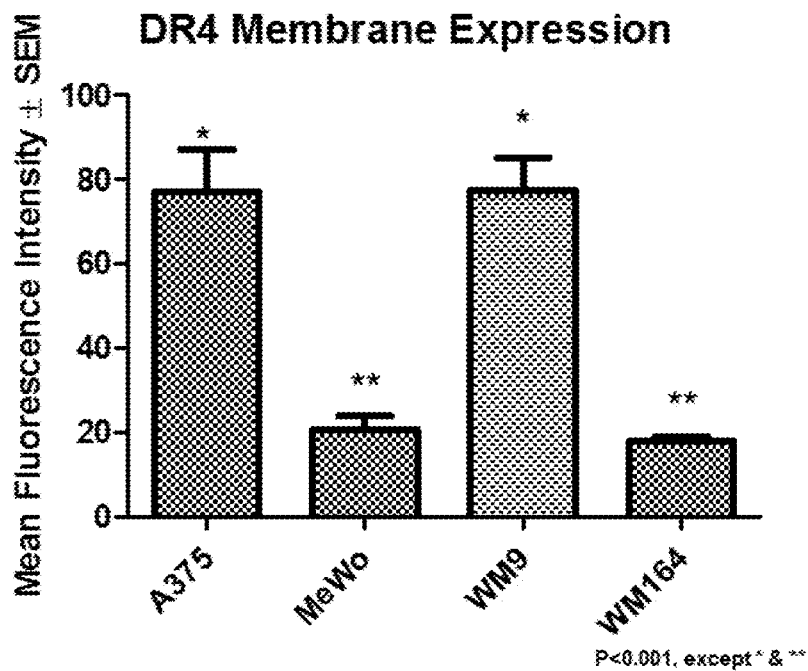
FIG. 1A shows membrane expression of rhTRAIL-binding receptors DR4 and DR5 on malignant melanomas (Mean Fluorescent Intensity (MFI)±SEM (n=9)).

While the general inventive concepts are susceptible of embodiment in many different forms, there are shown in the drawings, and will be described herein in detail, specific embodiments thereof with the understanding that the present disclosure is to be considered an exemplification of the principles of the general inventive concepts. Accordingly, the general inventive concepts are not intended to be limited to the specific embodiments illustrated herein.

rhTRAIL is the optimized form of the cytokine TRAIL consisting of only the biologically active C-domain. TRAIL is expressed by a number of immune effector cells such as monocytes and natural killer cells and is essential in regulating homeostasis through induction of apoptosis of aberrant cells. The application of rhTRAIL as an anti-cancer therapy shows great promise due to its ability to selectively induce apoptosis in a broad range of tumor types while showing minimal toxicity to normal non-transformed cells. While not wishing to be bound by theory, the mechanism of cancer cell specific rhTRAIL-induced apoptosis is through the binding of two pro-apoptotic DRs, DR4 and DR5 that are more abundantly expressed on cancer cells compared to normal healthy cells. Binding of rhTRAIL to DR4 and/or DR5 initiates the extrinsic pathway of apoptosis characterized by an intracellular caspase cascade involving the proteolytic cleavage of pro-enzymes into their activated form. At the end of the cascade, executioner caspases are activated and carry out the hallmark events of apoptosis including DNA fragmentation, cell shrinkage and cytoplasmic budding into apoptotic bodies.

rhTRAIL-resistance can be attributed to multitude of different sources but expression of rhTRAIL-binding receptors DR4 and DR5 is a major regulatory point for rhTRAIL-sensitivity. Consequently, the membrane expression of DR4 and DR5 are markers for characterizing a patient's sensitivity to rhTRAIL and therefore discriminate which patients would benefit from rhTRAIL-therapy from those who will not.

As previously mentioned, the compositions and methods described herein are based, in large part, on the dual discoveries that rhTRAIL sensitivity can be rapidly and reproducibly characterized, and that rhTRAIL-resistance can be abrogated through the administration of particular naturally-derived polyphenols (i.e., quercetin). Treatment with quercetin can modulate cellular components responsible for rhTRAIL-resistance. Thus, rhTRAIL-resistant malignant melanomas are sensitized by quercetin. Quercetin action is manifested by the upregulation of rhTRAIL-binding receptors DR4 and DR5 on the surface of cancer cells and by increased rate of the proteasome-mediated degradation of the anti-apoptotic protein FLIP. Thereby, cells are more susceptible to apoptosis when exposed to rhTRAIL.

The term "individual" as used herein, refers generally to an infant, toddler, child, or adult. Most often the term refers to a mammal, including a human.

The terms "susceptible" and "at risk" as used herein, unless otherwise specified, mean having little resistance to a certain condition or disease, including being genetically predisposed, having a family history of, and/or having symptoms of the condition or disease. The terms specifically refer to individuals having a greater risk or susceptibility than the population as a whole, including having a greater risk or susceptibility than subpopulations (e.g., all adults).

The terms "modulating" or "modulation" or "modulate" as used herein, unless otherwise specified, refer to the targeted movement of a selected characteristic.

The term "ameliorate" as used herein, unless otherwise specified, means to eliminate, delay, or reduce the prevalence or severity of symptoms associated with a condition.

The term "an effective amount" is intended to qualify the amount of a functional ingredient needed to modulate and/or ameliorate a condition or symptom. A "therapeutically effective amount" refers to an amount effective, at dosages and for periods of time necessary, to achieve the desired therapeutic result. A therapeutically effective amount can vary according to factors such as the disease state, age, sex, and weight of the individual, and the ability of the functional ingredient (e.g., rhTRAIL or quercetin) to elicit a desired response in the individual or tissue. A therapeutically effective amount is also one in which any toxic or detrimental effects of the composition are outweighed by the therapeutically beneficial effects. In certain exemplary embodiments, a therapeutically effective amount of a polyphenol is the amount or dose of which leads to rhTRAIL sensitivity of a cell or cell sample from an individual.

The term "rhTRAIL sensitivity" as used herein, unless otherwise specified, refers to the vulnerability of a particular cell or grouping of cells to rhTRAIL-induced apoptosis. The term generally refers to the membrane expression of certain receptors and/or to the ratio of certain proapoptotic receptors to anti-apoptotic receptors. In certain exemplary embodiments, the term refers to the amount (e.g., membrane expression) of a receptor selected from DR4, DR5, and combinations thereof. The amount may be determined by comparison with a known standard, but in certain embodiments, a cell or group of cells is rhTRAIL sensitive if the amount of a receptor selected from DR4, DR5, and combinations thereof is at least 1.5 times that of the standard, including 1.5 times to 6 times, including 1.5 times to 4 times, and including 2 to 4 times the level of a standard control cell. In certain exemplary embodiments, a cell or group of cells is rhTRAIL sensitive if: the membrane expression of DR4 is approximately 4-fold that of normal, the membrane expression of DR5 is approximately 2-fold that of normal, or a combination of both. Those of ordinary skill in the art will readily understand methods to determine and compare cell membrane receptor levels. One method for determining the basal level of membrane expression is to compare or normalize the value to that of the expression level of rhTRAIL-resistant non-cancerous melanocytes. Another example would be to use both established cancer cell lines and individual samples, to determine a clinical reference range of DR expression as a measure of suitability for rhTRAIL-treatment. Such range would be used to establish the values for a diagnostic test according to the general inventive concepts.

The terms "treating" and "treatment" as used herein, unless otherwise specified, includes delaying the onset of a condition, reducing the severity of symptoms of a condition, or eliminating some or all of the symptoms of a condition.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the general inventive concepts shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The compositions and methods may comprise, consist of, or consist essentially of the essential elements of the compositions and methods as described herein, as well as any additional or optional element described herein or otherwise useful in therapeutic treatments.

The molecular characterization of cancerous cells or tumors allows for the application of appropriate anti-cancer treatments tailored to a particular individual. Personalized cancer treatments are critical to customize therapies to individuals resulting in increased effectiveness while minimizing negative side effects. Individualized cancer plans can be applied to the clinical utilization of rhTRAIL as an anti-cancer therapeutic. The development of a test to identify patients that would benefit from rhTRAIL-based treatments is key to the successful clinical application of rhTRAIL.

Accordingly, in certain exemplary embodiments, the general inventive concepts are directed to an in vitro test to analyze one or more cells isolated from an individual (i.e., tumor cells or cells from tissue believed to be cancerous) for the membrane expression of death receptors (DRs) to determine their suitability for rhTRAIL-treatment (i.e., rhTRAIL sensitivity). Surprisingly, a correlation between DR membrane expression (in particular, DR4 and DR5) and rhTRAIL-sensitivity has been discovered. The membrane expression of DR4 and DR5 was examined through staining with anti-DR4 and DR5 followed by fluorescence-activated cells sorting (FACS). rhTRAIL-sensitivity was determined through Annexin-V and PI staining and western blotting post rhTRAIL-treatment. The data presented herein show that a flow cytometry-based assay for the analysis of isolated cells, including tumor cells, for DR membrane expression is effective. By first determining a patient's susceptibility to rhTRAIL-based treatments (rhTRAIL sensitivity), overall treatment can be improved.

As shown in the Figures and described in the Examples below, heterogeneity in rhTRAIL-sensitivity was seen in the panel of four malignant melanoma lines analyzed (see Example 1). In response to rhTRAIL-treatment, two out of the four lines were sensitive to rhTRAIL-induced apoptosis and two were resistant. In rhTRAIL-sensitive lines, A375 and WM9, the hallmark events of apoptosis, generation of apoptotic cells (Annexin-$V^+$ cells) and the fragmentation of the DNA repair enzyme PARP, occurred. However, these events did not transpire in rhTRAIL-resistant lines, MeWo and WM164, after exposure to rhTRAIL. The mechanism of rhTRAIL-induced apoptosis is mediated through the activation of the extrinsic pathway of apoptosis. The extrinsic apoptotic pathway is initiated by the binding of rhTRAIL to DR4 and/or DR5 followed by the subsequent activation of initiator caspase, caspase 8, from its pro-form procaspase 8. Caspase 8 can then cleave and activate downstream executioner caspases which ultimately carry out the events of apoptosis.

The Examples show that rhTRAIL is able to efficiently activate the extrinsic pathway of apoptosis in rhTRAIL-sensitive melanoma lines but not in rhTRAIL-resistant lines. This is evidenced by the formation of caspase 8 in rhTRAIL-sensitive lines, A375 and WM9, but not in rhTRAIL-resistant lines, MeWo and WM164.

Research has uncovered numerous mechanisms cancer cells use to evade rhTRAIL-induced apoptosis. One mechanism of rhTRAIL-resistance is mediated by the upregulation of anti-apoptotic proteins termed inhibitors of apoptosis proteins (IAPs), specifically cFLIP, XIAP, cIAP and survivin, which inhibit caspase activity and prevent cell death. Likewise, the equilibrium between pro- and anti-apoptotic members of the Bcl-2 family play an important role in regulating rhTRAIL-sensitivity. Overexpression of anti-apoptotic proteins, Bcl-2 and Bcl-xL, correlate highly with rhTRAIL-resistance. While, downregulation of pro-apoptotic Bcl-2 proteins, Bax and Bak, render cells resistant to rhTRAIL. Lastly, the optimum expression of pro-apoptotic rhTRAIL-receptors is indispensable in promoting apoptosis. rhTRAIL is known to bind to five receptors: two pro-apoptotic and three anti-apoptotic. Pro-apoptotic receptors, DR4 and DR5, contain cytoplasmic death domains through which rhTRAIL can initiate apoptosis. Anti-apoptotic receptors, decoy receptor 1 (DcR1), decoy receptor 2 (DcR2) and osteoprotegerin (OPG), act as antagonistic receptors. These receptors lack an intracellular death domain and do not appear to transmit an apoptotic signal upon rhTRAIL-binding.

Finding a predictive marker for rhTRAIL-sensitivity has proved challenging due to the extreme complexity of rhTRAIL-resistance. However, the membrane expression of DRs holds the most promise. Since DRs are at the most apical part of the rhTRAIL-induced apoptotic pathway without adequate levels of membrane-bound DRs there can be no induction of apoptosis regardless of other anti-apoptotic factors. Originally, the differential expression of pro-verses anti-apoptotic receptors was thought to be the cause for the difference in rhTRAIL-sensitivity. However, studies have shown that the distribution between pro- and anti-apoptotic receptors does not correlate with sensitivity. Additionally, although mRNA for DR4 and DR5 is present in the vast majority of cancer cells, due to post-translational modifications and intracellular trafficking, total receptor expression does not reflect the functional membrane expression of DR4 and DR5. Therefore, Applicant believes the best reflection of rhTRAIL-sensitivity is the amount of DRs on the cancer cell membrane. For measuring DR4 and DR5, there are already sensitive and specific fluorescent antibodies commercially available. Finally, the utilization of a flow cytometry-based technique allows for the rapid interrogation of isolated cells with little sample preparation that can be easily integrated into clinical testing.

Results presented herein show a direct correlation between DR expression and sensitivity to rhTRAIL-induced apoptosis. rhTRAIL-resistant lines, MeWo and WM164, had significantly less DR4 and DR5 expressed on their membrane compared to the rhTRAIL-sensitive lines, A375 and WM9. On average the rhTRAIL-sensitive melanoma lines had nearly four-fold more DR4 membrane expression. For DR5, on average the rhTRAIL-sensitive melanoma lines had over two-fold more membrane expression than rhTRAIL-resistant lines.

rhTRAIL-sensitive cancers have significantly higher membrane expression of both DR4 and DR5 than rhTRAIL-resistant cells. Yet, even resistant cells express some levels of DR4 and DR5; although, they do not undergo apoptosis in response to rhTRAIL-treatment. Applicants have shown that the non-transformed counterpart of melanomas, melanocytes, are resistant to rhTRAIL-induced apoptosis even though they do express DR4 and DR5 on their cell membrane. However, normal melanocytes have a much lower membrane expression of both DR4 and DR5 as compared to rhTRAIL-sensitive melanoma cells. For a cell to undergo rhTRAIL-induced apoptosis a threshold for apoptosis activation must be achieved. In order for a cell to activate the process of apoptosis a certain amount of caspase 8 must be activated through the binding of DR4 and/or DR5 by rhTRAIL. Accordingly, in certain embodiments, cells are rhTRAIL sensitive when expressing a threshold amount of DR4, DR5, or a combination of both on the cell membrane.

The data presented herein shows that a two-fold increase in DR expression compared to normal cells is enough to render cells (including cancer cells) sensitive to rhTRAIL-induced apoptosis (i.e., the cells are rhTRAIL sensitive).

Utilizing a flow cytometry-based technique, Applicants show the value of measuring DR membrane expression to predict rhTRAIL-sensitivity on established malignant melanoma cell lines. This technique can be easily translated into a clinical test to characterize tumor cells isolated from individuals, applicable to both solid and hematological cancers. The use of flow cytometry to analyze solid tumors is relatively novel and includes samples from surgical specimens, fine needle aspirations or frozen or paraffin-embedded tissues. Analysis of solid tissue involves the disaggregation of the sample into a single cell suspension. Those of skill in the art will recognize that there are a variety of ways to accomplish this, including either mechanically or with enzymes such as collegenase or a combination of both, for example. Flow cytometry in the analysis and diagnosis of hematological cancers such as leukemia and lymphoma is well established and is currently clinically utilized. The application of multiparameter flow cytometry allows for the rapid and sensitive detection of abnormal cells in a tumor sample or whole blood. Abnormal cells are identified by the presence of antigens such as clusters of differentiation (CD) that differs significantly from their normal counterpart. Therefore, DR4 and DR5 can be easily added to the panel of markers used to diagnosis these cancers.

Although the application of rhTRAIL as an anti-cancer therapeutic holds great promise, the clinical use has been limited due to the heterogeneity seen in rhTRAIL-sensitivity among cancers. This is especially prevalent in cases of advanced metastatic malignant melanoma. Nearly two-thirds of melanoma cells are resistant to rhTRAIL-induced apoptosis, including melanomas directly isolated from cancer patients. Melanoma rhTRAIL-resistance can be attributed to a number of different causations. One of which is the decreased membrane expression of pro-apoptotic rhTRAIL-binding receptors DR4 and DR5. Thus, it would be beneficial to identify one or more agents with the ability to increase expression of pro-apoptotic rhTRAIL-binding receptors DR4 and DR5 in otherwise resistant cells (i.e., sensitize the cells to rhTRAIL therapy).

Quercetin is a polyphenol of the flavonoid group and is found in a wide variety of sources ranging from onions and apples to red wine. As a pleiotropic molecule, quercetin exhibits anti-cancer effects on a number of different pathways such as cell survival pathways, cell cycle arrest, upregulation of tumor suppressor genes, downregulation of anti-apoptotic proteins and pro-apoptotic pathways. It has been demonstrated that quercetin is able to downregulate a number of anti-apoptotic proteins that promote rhTRAIL-resistance, specifically FLIP, Mcl-1 and survivin. The ability of quercetin to sensitize rhTRAIL-resistant malignant melanomas has not previously been evaluated. The data presented herein demonstrate the ability of the combination rhTRAIL plus quercetin to overcome the intrinsic resistance of metastatic malignant melanomas to rhTRAIL.

As previously mentioned, melanoma cell lines MeWo and WM164, both derived from cases of metastatic malignant melanoma, are among the melanoma cell lines resistant to rhTRAIL-induced apoptosis. Even following treatment with extremely high concentrations of rhTRAIL no apoptosis was observed. This was further evidenced by the lack of apoptotic Annexin-V$^+$ cells, cleaved PARP or activation of any key proteins in either the extrinsic or intrinsic pathways. However, as shown herein, the administration of quercetin was able to negate the rhTRAIL-resistance of both MeWo and WM164. Treating at sub cytotoxic concentrations of both single agents, the combination of rhTRAIL plus quercetin was able to induce apoptosis in both cell lines apparent by the significant formation of Annexin-V$^+$ cells, PARP cleavage and activation of executioner caspases 3, 6 and 7, dose-dependently with respect to quercetin. The combination treatment allowed for the activation of the extrinsic apoptotic pathway as noted by the formation of caspase 8. It is interesting to note that in WM164 and not in MeWo the intrinsic pathway was activated through the co-treatment mediated by formation of tBID followed by the release of cytochrome c from the mitochondria and the activation of caspase 9. The general caspase inhibitor Z-VAD-FMK was used to assess the indispensable role of enhanced caspase activity in the sensitization of rhTRAIL-resistant malignant melanomas through the addition of quercetin. The data presented herein clearly show that caspase activation is required to mediate the apoptosis process and is only induced in the presence of quercetin and rhTRAIL.

Of the most significance is that the addition of quercetin to rhTRAIL allowed for the activation of rhTRAIL-mediated extrinsic apoptotic pathway. Accordingly, in certain exemplary embodiments, the compositions and methods according to the general inventive concepts contemplate co-administration of quercetin with a rhTRAIL regimen. This activation is demonstrated by the cleavage of pro-caspase 8 to caspase 8, a marker for rhTRAIL-induced apoptosis. The activation of caspase 8 in only the co-treatment group implies that quercetin plays a role in regulating cellular components responsible for controlling rhTRAIL-sensitivity, demonstrating the surprising synergy of the co-administration.

To understand the mechanism of the sensitization of rhTRAIL-resistant malignant melanomas by quercetin, the effects of quercetin on the most apical parts of the extrinsic pathway were evaluated. Additionally, rhTRAIL interactions with two antagonist receptors, decoy receptor (DcR) 1 and DcR2. These anti-apoptotic receptors lack an intracellular death domain and cannot transmit an apoptotic signal upon rhTRAIL-binding. Originally, the differential expression of pro-apoptotic compared to anti-apoptotic receptors was thought to be the cause for differences in rhTRAIL-sensitivity. However, studies have shown that the distribution between pro-apoptotic and anti-apoptotic receptors does not correlate with sensitivity.

Multiple reports claim that low levels of DRs on the membrane of cancer cells confers rhTRAIL-resistance. As previously mentioned, it is shown herein that rhTRAIL-resistant melanomas MeWo and WM164 have two-fold less membrane expression of both DR4 and DR5 compared to rhTRAIL-sensitive melanomas and the melanoma's benign counterpart melanocytes. Nonetheless, the membrane expression of both DR4 and DR5 can be upregulated on melanoma cells via quercetin. While not wishing to be bound by theory, it appears the mechanism in which quercetin executes the upregulation in melanoma cells differs between DR4 and DR5. DR expression can be regulated transcriptionally or through post-translational modifications including protein glycosylation, trafficking and endocytosis. The instant examples show that quercetin promotes DR5 upregulation on the membrane of melanoma WM164 cells as a consequence of quercetin-stimulated gene transcription. This is illustrated by the correlation between the increased DR5 membrane expression and an increase in the total DR5 protein and mRNA levels, dose-dependently in response to quercetin. Several studies have shown that quercetin is capable of upregulating DR5 on the membrane of cancer cells mediated through the increased activity of transcription factors including p53, CHOP and SP1. However, the transcriptional regulation of DR5 by quercetin has never been evaluated in melanoma cells. A p53-mediated mechanism can be excluded because WM164 has an inactivating Y220C mutation in the p53 gene yet experienced DR5 upregulation.

Conversely, the robust upregulation of DR4 on the membrane of the melanoma cells was not by means of enhanced transcription. This is evident by the absence of an increase in the total protein and mRNA of DR4 in response to quercetin-treatment. Previous studies have shown that total protein and mRNA levels do not correlate with the functional membrane expression of DRs. Studies show that some melanoma cells, despite the presence of mRNA, lack DR4 membrane expression but have high levels of the receptor within the cytoplasm. Additionally, immunohistochemistry staining of DR4 reveals that the receptor can be localized to the trans-Golgi network in melanoma cells. The translocation of DRs from the trans-Golgi network to the plasma membrane is a complex system regulated by cargo transport proteins such as Arf and ARAP1. Malfunctions in this pathway can result in DR surface deficiency and increased localization to the cytoplasm. It is shown that both melanoma lines have substantial levels of DR4 within the cytoplasmic portion of the cell which substantially decreases upon quercetin-treatment. While not wishing to be bound by theory, Applicants postulate that quercetin promotes the vesicular movement of DR4 from the cytoplasm or the trans-Golgi network to the cellular membrane. The ability of quercetin to promote the DR4 upregulation on the cancer cell membrane is an important finding. The quercetin-mediated upregulation of DR4 has never been described and warrants thorough examination of the exact mechanism by which quercetin promotes this movement.

What is interesting to note is that although rhTRAIL-resistant malignant melanomas, MeWo and WM164, possess less DRs than their sensitive melanoma counterparts, they still express some quantities of DR4 and DR5. However, the rhTRAIL-resistant melanomas do not express the requisite level of DRs required to overcome the apoptotic threshold of the cancer cell. To overcome this threshold a certain amount of caspase 8 must be activated and this is mediated by the binding of rhTRAIL to DR4 or DR5. Without sufficient DR membrane expression there can be no induction of apoptosis. Through the addition of quercetin the membrane concentration of DRs can be increased allowing for enough caspase 8 to be activated to overcome the apoptotic threshold.

Moreover, the binding of rhTRAIL to DR4 and/or DR5 results in the trimerization of the receptors leading to the assembly of the intracellular death-inducing signaling complex (DISC). At the DISC, the adaptor protein, Fas-associated death domain (FADD), acts as a bridge between the death-receptor complex and the death effector domain (DED) of the initiator caspase, procaspase 8. Induced proximity results in the autoproteolytic cleavage of procaspase 8 into its active form, caspase 8. However, the anti-apoptotic protein FLIP will compete for FADD binding, decreasing the formation of caspase 8 and impeding the pro-apoptotic signal generated by rhTRAIL-binding. This is a result of the homology between FLIP and procaspase 8, both possessing a DED, yet FLIP lacks caspase activity. The ratio between caspase 8 and FLIP is a major regulator of rhTRAIL-sensitivity. Although quercetin has no direct effect on pro-caspase 8 levels, the examples show downregulation of FLIP in the presence of quercetin which resulted in an increase in the concentration of the pro-apoptotic procaspase 8. Increase in procaspase 8 resulted in the sensitization of previously resistant melanoma cancer cells to rhTRAIL. FLIP levels are maintained by a balance between transcription and degradation mediated by the ubiquitin-proteasome degradation system. The examples show that quercetin promotes the downregulation of FLIP mediated through degradation by the proteasome. This is apparent by the inhibition of the quercetin-mediated FLIP downregulation when a proteasome inhibitor is applied. Additional studies have also shown that quercetin is able to downregulate FLIP mediated by the proteasome however this has never been shown in a melanoma model.

The examples provide insight into the molecular mechanisms in which rhTRAIL-induced apoptosis can be modulated by quercetin in advanced metastatic malignant melanomas. The application of rhTRAIL is far superior to other therapeutics due the selectivity of rhTRAIL for only cancer cells while exhibiting no harm to healthy cells. This selectively will result in potent anti-tumor activity with minimal side effects for the patient. However, the presentation of resistance limits the application of rhTRAIL. Nonetheless, resistance can be overcome through the co-treatment of rhTRAIL with quercetin. Quercetin's effect is translated by the combined action of the upregulation of both DR4 and DR5 on the cell membrane and the downregulation of the anti-apoptotic protein FLIP. As a result of the diverse effects of quercetin, its addition led to the successful sensitization of rhTRAIL-resistant malignant melanomas through co-treatment with rhTRAIL. In the end, the multiple targeted properties of quercetin make it a prime candidate for rhTRAIL co-treatment compared to compounds that only affect a singular cellular component.

Accordingly, in certain exemplary embodiments, the general inventive concepts relate to a pharmaceutical composition useful for ameliorating and/or treating cancer, including malignant melanoma. The composition may comprise an effective amount of rhTRAIL and, in certain instances, an effective amount of a polyphenol that increases the sensitivity of one or more cells to rhTRAIL. One such polyphenol is quercetin.

In certain exemplary embodiments, the general inventive concepts relate to a method of ameliorating and/or treating cancer, including malignant melanoma. The method comprises administering, to an individual in need thereof, a composition comprising an effective amount of rhTRAIL and, in certain instances, an effective amount of a polyphenol that increases the sensitivity of one or more cells to rhTRAIL. One such polyphenol is quercetin.

Further, in certain exemplary embodiments, the general inventive concepts relate to a method of increasing the rhTRAIL sensitivity of one or more target cells. The method comprises identifying one or more cells having a low or reduced rhTRAIL sensitivity and administering an effective amount of a polyphenol thereby increasing the sensitivity of one or more cells to rhTRAIL until the desired rhTRAIL sensitivity is achieved. One such polyphenol is quercetin.

Methods of Use

As previously mentioned, the rhTRAIL (and, in certain embodiments, quercetin) discussed herein can be incorporated into pharmaceutical compositions suitable for administration to an individual. In an exemplary embodiment, the pharmaceutical composition will comprise rhTRAIL and a polyphenol along with a pharmaceutically acceptable carrier. As used herein, "pharmaceutically acceptable carrier" includes any and all solvents, dispersion media, coatings, antibacterial, and antifungal agents, isotonic and absorption delaying agents, and the like that are physiologically compatible. Pharmaceutically acceptable substances include minor amounts of auxiliary substances such as wetting or emulsifying agents, preservatives or buffers, which enhance the shelf life or effectiveness of the functional ingredients.

The compositions as described herein may be in a variety of forms. These include, for example, liquid, semi-solid, and solid dosage forms, such as liquid solutions (e.g., injectable and infusible solutions), dispersions or suspensions, powders, liposomes, and suppositories. The preferred form depends on the intended mode of administration and therapeutic application. Typical preferred compositions are in the form of injectable or infusible solutions, such as compositions similar to those used for cancer therapies. One mode of administration is parenteral (e.g., intravenous, subcutaneous, intraperitoneal, intramuscular).

The rhTRAIL (and in certain embodiments, quercetin) described herein can be administered by a variety of methods known in the art, although for many therapeutic applications, the preferred route/mode of administration is either oral administration, intravenous injection, or infusion, or in certain instances, a combination thereof. The compositions can also be administered by intramuscular or subcutaneous injection.

As will be appreciated by those of skill in the art, the route and/or mode of administration will vary depending upon the desired results. In certain embodiments, the active compound may be prepared with a carrier that will protect the compound against rapid release, such as a controlled release formulation, including implants, and microencapsulated delivery systems. Additional active compounds can also be incorporated into the compositions.

Dosage regimens may be adjusted to provide the optimum desired response. For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. Dosage unit form as used herein refers to physically discrete units suited as unitary dosages for the individuals to be treated; each unit containing a predetermined quantity of active compound calculated to produce the desired therapeutic effect in association with the required pharmaceutical carrier.

The compositions, as described herein, can be administered to individuals that are "in need thereof," that is, to specific individuals that would particularly benefit by administration of the compositions. For example, a specific individual may be "in need of" the compositions as described herein if they are susceptible to (i.e., have one or more of a genetic predisposition, a family history of, and symptoms of the disease or condition) diseases and conditions that can impair/reduce function in one or more of the areas discussed herein. In particular, the compositions are useful for treating or ameliorating the symptoms of cancer, including malignant melanoma.

Based on the foregoing, because some of the method embodiments according to the general inventive concepts are directed to specific subsets or subclasses of identified individuals (that is, the subset or subclass of individuals "in need" of assistance in addressing one or more specific diseases or specific conditions noted herein), not all individuals will fall within the subset or subclass of individuals as described herein for certain diseases or conditions.

While particular embodiments are described herein, one of ordinary skill in the art will recognize that various other combinations of elements are possible and will fall within the general inventive concepts. Likewise, one of ordinary skill in the art will understand that the various embodiments of compositions and methods described herein are suitable for use in the methods described herein.

EXAMPLES

Example 1

Utilizing a panel of malignant melanoma cell lines, the correlation between DR membrane expression and rhTRAIL-sensitivity was evaluated. The membrane expression of DR4 and DR5 was examined through staining with anti-DR4 and DR5 followed by FACS. rhTRAIL-sensitivity was determined through Annexin-V and PI staining and western blotting post rhTRAIL-treatment.

A direct correlation between the membrane expression of DRs and rhTRAIL-sensitivity is shown. rhTRAIL-sensitive melanoma lines on average had nearly four-fold more DR4 and over two-fold more DR5 than rhTRAIL-resistant lines.

For a cancer cell to display rhTRAIL-sensitivity the optimum expression of DRs is essential. To overcome the apoptotic threshold cancer cells must express DRs over two-fold higher than their benign counterpart.

Methods:

Drugs and Chemicals. rhTRAIL was produced according to well defined and previously detailed protocols.

Cell Culture. Cells were incubated in a 90% humidified atmosphere with 5% $CO_2$ at 37° C. Human adult primary epidermal melanocytes (ATCC PCS-200-013) were maintained in Dermal Cell Basal Medium supplemented with an Adult Melanocyte Growth kit (ATCC PCS-200-042) and 1% Antibiotic/Antimycotic Solution. The malignant melanoma cell lines, A375 (ATCC CRL-1619), WM9 and WM164 were maintained in DMEM and MeWo (ATCC HTB-65) was maintained in RPMI, both supplemented with 10% Fetal Bovine Serum (FBS) and 1% Antibiotic/Antimycotic Solution. WM9 and WM164 were a kind gift from Dr. Daniel J. Lindner from the Cleveland Clinic Foundation, Cleveland, Ohio Malignant melanoma lines are derived from patient tumors. A375 was derived from an epithelial skin biopsy. MeWo, WM9 and WM164 are metastatic malignant melanomas isolated from the lymph nodes.

Death Receptor Membrane Expression. Untreated and rhTRAIL-treated cells were collected with enzyme-free phosphate-buffered saline (PBS)-based cell dissociation buffer (Gibco Life Technologies) and stained with mouse anti-human DR4 or DR5 conjugated to phycoerythrin (PE) (eBioscience). Briefly, $0.25 \times 10^6$ cells were incubated in 100 μl of staining buffer (2% FBS and 0.02% sodium azide in PBS) and 5 μl anti-DR4 or anti-DR5 for one hour on ice in the dark. As a negative control to account for non-specific antibody binding, all four melanoma lines were stained with mouse IgG1κ, the same antibody isotype as DR4 and DR5, under the same conditions. After incubation, cells were washed twice with staining buffer and resuspended in 500 μl of staining buffer and analyzed on BD FACS Canto II using Diva software (BD Bioscience, San Jose, Calif.).

Apoptosis Assay. Cells were trypsinized, harvested, washed twice with cold PBS and resuspended in 100 μl of Annexin-V binding buffer at a concentration of $1 \times 10^3$ cells/μl. According to manufacturer's protocol, cells were incubated with 5 μl of FITC-Annexin-V and propidium iodide (PI) for 15 minutes at room temperature in the dark (FITC-Annexin-V Kit Apoptosis Detection Kit I, BD Pharmingen). Stained cells were analyzed on BD FACS Canto II using Diva software. Single color controls (Annexin-V or PI only) were used to set up compensation and quadrants for FACS.

Western Blot Analysis. Total cell lysates were prepared using RIPA lysis buffer (Sigma) containing 150 mM sodium chloride, 1.0% Triton X-100, 0.5% sodium deoxycholate, 0.1% sodium dodecyl sulfate (SDS) and 50 mM Tris, pH 8.0 plus a 1× cocktail of protease inhibitors (Protease Inhibitor Cocktail Set I, Calbiochem). Cells were lysed for 30 minutes at 4° C. followed by centrifugation for 10 minutes at 10,000 rpm at 4° C. Protein concentrations were determined using BCA protein assay (Pierce). A 35 μg protein aliquot was mixed with 4× Laemmli's SDS sample buffer (0.02% Bromophenol Blue (BPB), 8% Beta-mercaptoethanol (BME), 8% SDS, 40% glycerol and 250 mM Tris-HCl, pH 6.8). Cell lysates were heated for five minutes at 100° C., resolved by 12% SDS-polyacrylamide gel electrophoresis (SDS-PAGE) and transferred to polyvinylidene fluoride (PVDF) membrane. The membrane was blocked with 5% non-fat milk or 5% BSA for ≥1 hour and incubated with primary antibodies for PARP and caspase 8 (Cell Signaling). After incubation, the membrane was incubated with secondary anti-rabbit or mouse horseradish peroxidase (HRP)-conjugated antibodies (Biorad). Proteins were visualized through development by enhanced chemiluminescence (ECL 2 Western Blotting Substrate, Pierce) and exposure on X-ray film. The blots were reprobed for β-actin to confirm equal protein loading.

Statistical Analysis. Student t-test was used to determined significance. P values less than 0.05 were deemed significant.

Figure 1B:
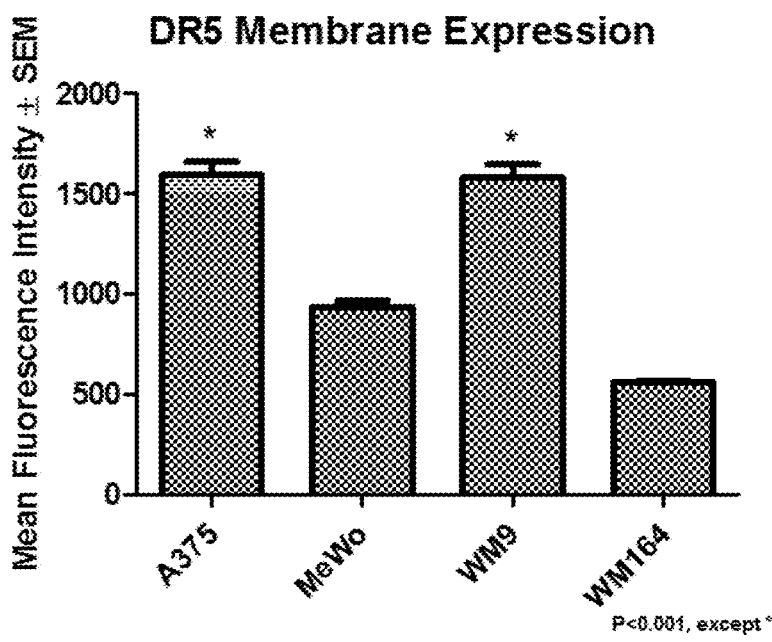
FIG. 1B shows membrane expression of DR5 (MFI±SEM (n=9)).
Figure 1C:
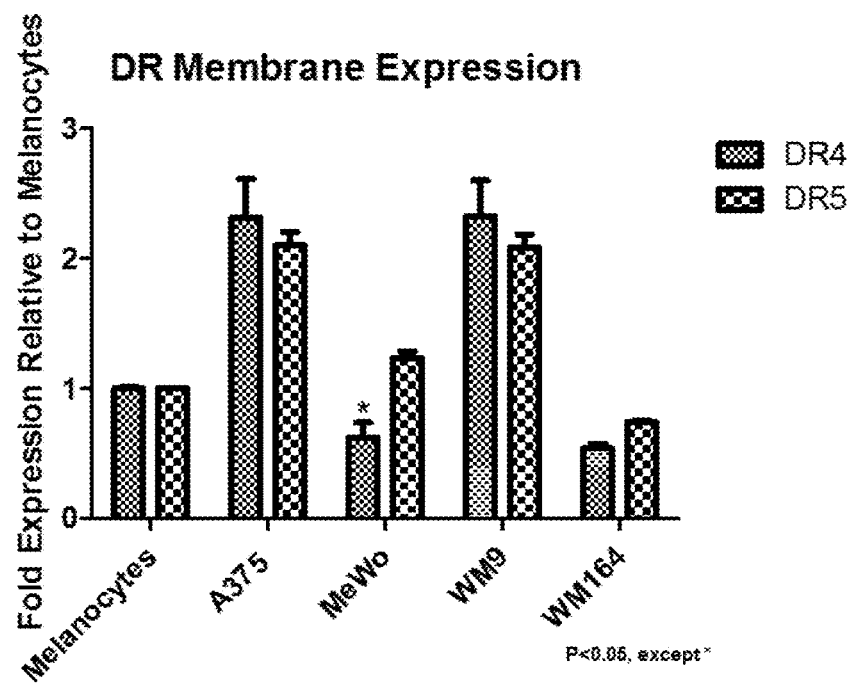
FIG. 1C shows melanoma DR expression normalized to non-cancerous melanocytes.

FIG. 1 shows membrane expression of Death Receptors. Specifically. membrane expression of rhTRAIL-binding receptors DR4 and DR5 on malignant melanomas. FIG. 1A: Membrane expression of DR4. Mean Fluorescent Intensity (MFI)±SEM (n=9). FIG. 1B: Membrane expression of DR5. MFI±SEM (n=9). FIG. 1C: Melanoma DR expression normalized to non-cancerous melanocytes.

Figure 2A:
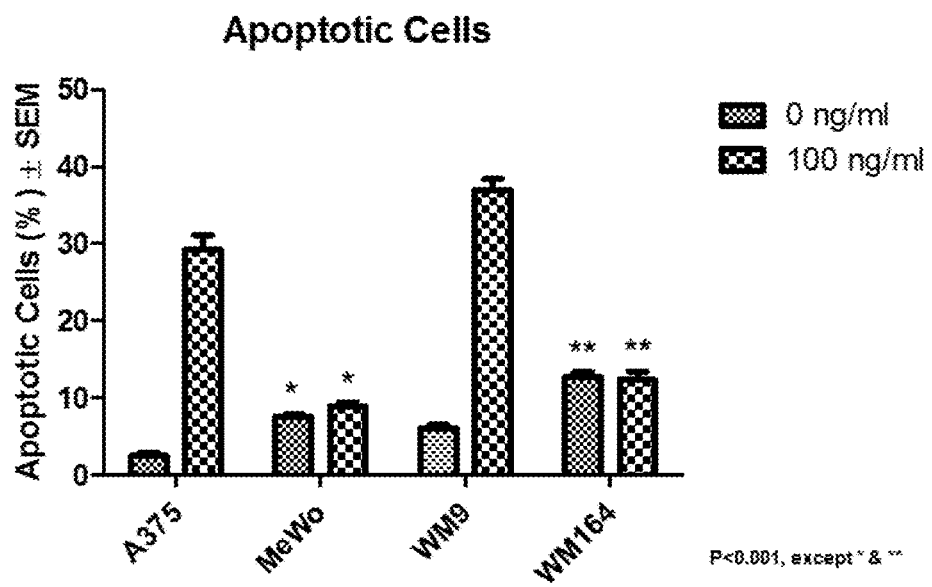
FIG. 2A shows the percent apoptotic cells±SEM (average of three independent assays (n=9))
Figure 2B:
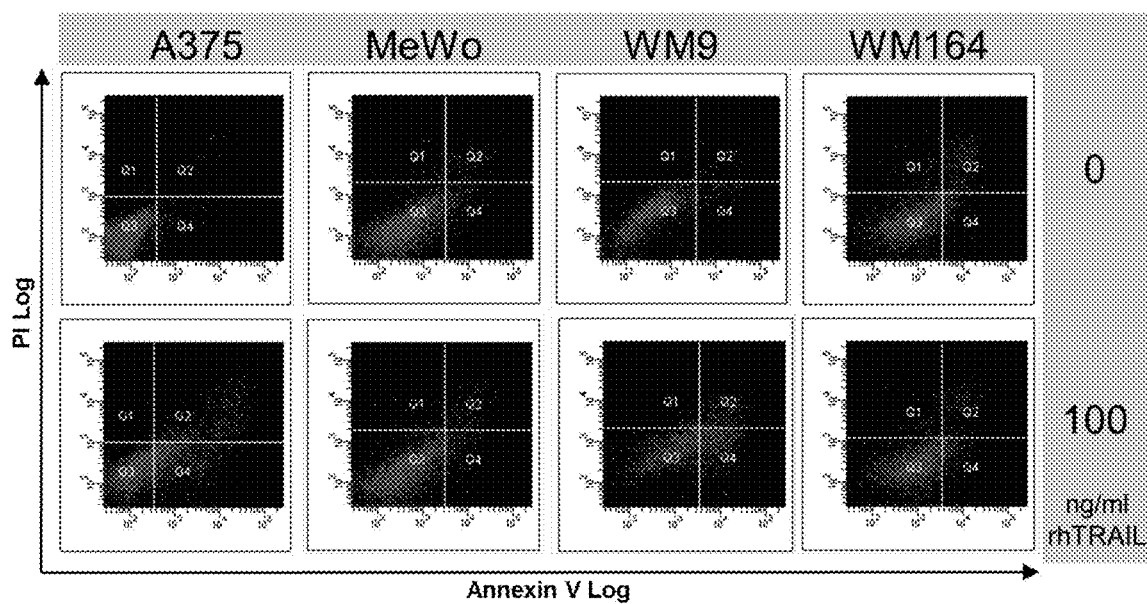
FIG. 2B shows a representative histogram.
Figure 2C:
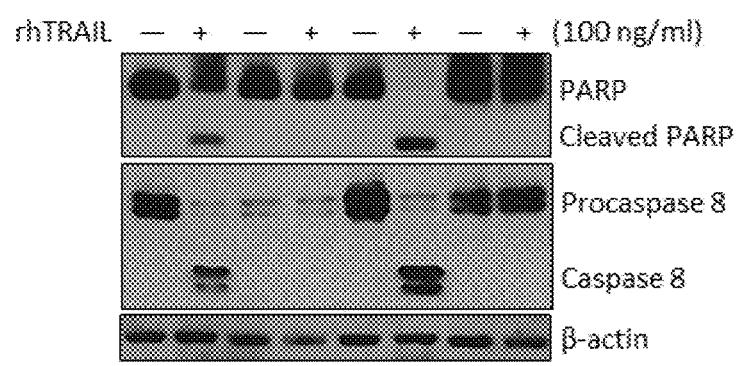
FIG. 2C shows melanoma lines±rhTRAIL subjected to western blot analysis and probed with anti-PARP or anti-caspase 8.

FIG. 2 shows rhTRAIL-sensitivity. FIG. 2A: Percent apoptotic cells±SEM. Average of three independent assays (n=9). FIG. 2B: Representative histogram. Lower left quadrant: Viable cells (Annexin⁻/PI⁻), Lower right quadrant: Early apoptotic cells (Annexin⁺/PI⁻), Upper right quadrant: Late apoptotic cells (Annexin⁺/PI⁺). FIG. 2C: Melanoma lines±rhTRAIL subjected to western blot analysis and probed with anti-PARP or anti-caspase 8. β-actin was used as a loading control for each membrane. Representative β-actin is depicted.

Melanoma Death Receptor Expression: The membrane expression of DR4 and DR5 was examined on a panel of malignant melanoma lines, A375, MeWo, WM9 and WM164, through staining with saturating amounts of anti-human DR4 and DR5 conjugated to PE followed by FACS analysis. Comparing the membrane expression of DRs for each line, two of the lines, A375 and WM9, on average had nearly four-fold more membrane expression of DR4 and over two-fold more DR5 compared to melanoma lines, MeWo and WM164 ($P<0.001$) (FIGS. 1A & 1B). Previously, it was shown that the non-transformed counterpart of melanomas, melanocytes, also express both DR4 and DR5 but do not undergo apoptosis when challenged with rhTRAIL even at concentrations as high as 1 μg/ml. The melanoma DR membrane expression was normalized to the expression of the rhTRAIL-resistant non-cancerous melanocytes (FIG. 1C). A375 and WM9 lines expressed DR4 on the membrane over two-fold more than melanocytes ($P<0.05$); whereas, MeWo expressed DR4 at the same level ($P>0.05$) and WM164 expressed DR4 at only half the amount ($P<0.05$). For DR5, A375 and WM9 lines had over two-hold higher membrane expression ($P<0.05$); while, MeWo had slightly more DR5 and WM164 had slightly less than the melanocytes ($P<0.05$).

Melanoma rhTRAIL-Sensitivity: To test rhTRAIL-sensitivity, malignant melanoma lines were treated with and without 100 ng/ml of rhTRAIL for 72 hours. Prior to treatment, control experiments were done to determine the optimal conditions for rhTRAIL-treatment (data not shown). The treatment of 100 ng/ml for 72 hours was selected to best distinguish between rhTRAIL-sensitive and rhTRAIL-resistant melanomas. Post-treatment cells were analyzed for induction of apoptosis through FITC-Annexin-V and PI staining followed by FACS analysis (FIGS. 2A & 2B). Two of the four lines, A375 and WM9, underwent apoptosis in response to rhTRAIL-treatment, whereas, the other two, MeWo and WM164, did not. In response to rhTRAIL-treatment, A375 formed 29.2±2.0% apoptotic cells ($P<0.001$) and WM9 formed 36.9±0.5% apoptotic cells ($P<0.001$), however, MeWo and WM164 did not form significant apoptotic cells as compared to the control (P>0.05). To confirm the event of rhTRAIL-induced apoptosis, western blotting was employed using antibodies to various components of the apoptotic cascade. rhTRAIL significantly induced apoptosis in A375 and WM9 noted by the fragmentation of the DNA repair enzyme Poly-(ADP) Ribose Polymerase (PARP) but this did not occur in rhTRAIL-resistant melanomas, MeWo and WM164 (FIG. 2C). Treatment with rhTRAIL was able to effectively initiate the extrinsic pathway of apoptosis in rhTRAIL-sensitive lines, A375 and WM9, as indicated by the cleavage of procaspase 8 to caspase 8 which was not present in rhTRAIL-resistant lines, MeWo and WM164, post-rhTRAIL-treatment (FIG. 2C).

Example 2

The in vitro sensitivity of metastatic malignant melanoma cell lines MeWo and WM164 to rhTRAIL were tested by treating with increasing concentrations of rhTRAIL (5 ng/ml to 1 μg/ml) for 72 hours followed by Annexin-V and PI staining and FACS analysis (FIGS. 1 A-C).

Methods

Drugs and Chemicals: rhTRAIL was produced according to well-defined and previously detailed protocols. Quercetin dihydrate (Calbiochem) was dissolved in Polyethylene Glycol (PEG)-400 (Fisher Scientific). MG132 (Calbiochem) was dissolved in dimethyl sulfoxide (DMSO). General caspase inhibitor Z-VAD-FMK (Calbiochem) was dissolved in DMSO.

Cell Culture. WM164 cells were maintained in DMEM and MeWo cells were maintained in RPMI, both supplemented with 10% Fetal Bovine Serum (FBS) and 1% Antibiotic/Antimycotic Solution. Cells were incubated in a 90% humidified atmosphere with 5% $CO_2$ at 37° C.

Apoptosis Assay. Apoptotic cells were identified using FITC-Annexin-V Kit Apoptosis Detection Kit I (BD Pharminogen) and previously described methods.

Western Blot Analysis. Total cell lysates were analyzed for levels of PARP, caspase 8, caspase 3, Bid, caspase 9, caspase 6, caspase 7, FLIP, DR4 and DR5 and the cytosolic cellular fraction was analyzed for cytochrome C (Cell Signaling) using previously described western blotting techniques.

Death Receptor Membrane Expression. The cell surface expression of DR4 and DR5 were determined according to previously described methods. For the permeabilization experiments, after the first antibody incubation cells were fixed in 4% paraformaldehyde for 10 minutes at room temperature and permeabilized with 0.1% saponin for 5 minutes at room temperature. Cells were then incubated with anti-IgG1κ, DR4 or DR5 for 30 minutes in the saponin buffer and analyzed by FACS. To calculate the cytoplasmic DR expression, the permeablized cells representing the total DR expression was subtracted from the unpermeablized cells representing membrane-bound DRs.

Reverse Transcription-PCR. Total RNA was extracted using TRIzol reagent (Ambion) and treated with DNase according to manufacturer's protocol (Invitrogen Deoxyribonuclease I, Amplification Grade). RT-PCR was performed following the manufacturer's protocol (Invitrogen SuperScript III One-Step RT-PCR System with Platinum® Taq DNA Polymerase). Human DR5 mRNA was amplified using the forward primer 5'-GGGAGCCGCTCATGAG-GAAGTTGG-3' and the reverse primer 5'-GGCAAGTCTCTCTCCCAGCGTCTC-3'. For DR4, forward primer 5'-GAGCAACGCAGACTCGCT-3' and the reverse primer 5'-TCACTCCAAGGACACGGC-3' were used. For FLIP, forward primer 5'-CTTGGCCAAT-TTGCCTGTAT-3' and the reverse primer 5'-CCCATGAA-CATCCTCCTGAT-3' were used. For β-actin, the forward primer 5'-TGACGGGGTCACCCACACTGTGCC-3' and the reverse primer 5'-CTG-CATCCTGTCGGCAATGCCAG-3' were used. cDNA synthesis was performed at 60° C. for 30 minutes using the Applied Biosystems GeneAmp PCR System 9700. The PCR cycling conditions (30 cycles) were as follows: denature for 2 minutes at 94° C., anneal for 30 seconds at 55° C. for FLIP and DR4 and 65° C. for DR5 and β-actin, extend for 1 minute and 30 seconds at 68° C., and execute a final extension for 10 minutes at 68° C. Reaction products were analyzed on 1.2% agarose gels. The bands were visualized by ethidium bromide and an UV.

The computer readable sequence listing entitled 2743304085_ST25.txt, created on Aug. 21, 2018, which is 1.66 KB in size, is hereby incorporated by reference herein.

Statistical Analysis. Student t-test was used to determined significance. P values less than 0.05 were deemed significant.

rhTRAIL sensitivity: Both melanoma lines showed complete resistance to rhTRAIL-induced apoptosis. Treatment with rhTRAIL, even at the highest tested treatment concentration of 1 μg/ml, did not result in the formation of apoptotic cells as indicated by the lack of Annexin-$V^+$ and/or Annexin-V+ and $PI^+$ cells as compared to the control (P>0.05).

FIG. 3 demonstrates rhTRAIL sensitivity of malignant melanomas MeWo and WM164 to rhTRAIL in vitro. FIG. 3A: average of three independent assays±SEM. FIG. 3B: Representative histogram of MeWo. FIG. 3C Representative histogram of WM164. Lower left quadrant: Viable cells (Annexin$^-$/PI$^-$), Lower right quadrant: Early apoptotic cells (Annexin$^+$/PI$^-$), Upper right quadrant: Late apoptotic cells (Annexin$^+$/PI$^+$). 3D: MeWo and 3E: WM164±rhTRAIL subjected to western blot analysis and probed with anti-PARP, caspase 8, Bid, cytochrome c, caspase 9, caspase 3, caspase 6 and caspase 7. f3-actin was used as a loading control for each membrane. Representative f3-actin is depicted.

Figure 3A:
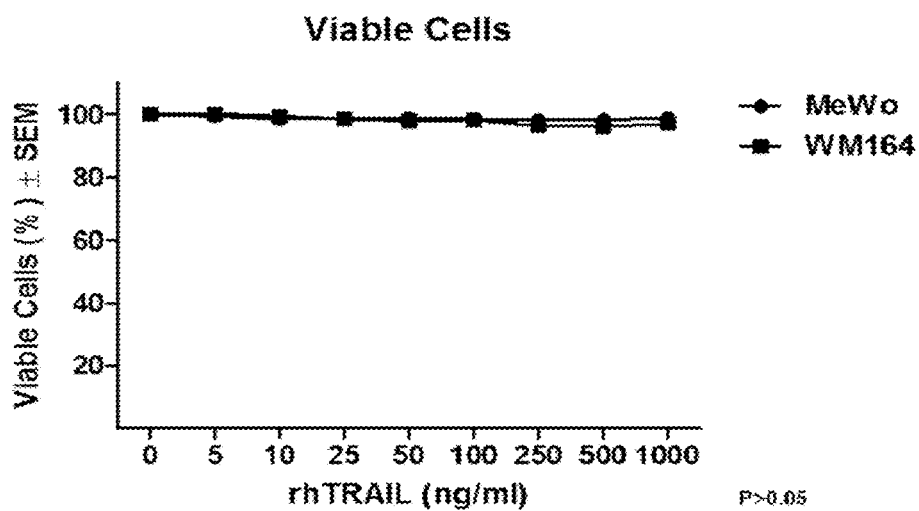
FIG. 3A shows the sensitivity of malignant melanomas MeWo and WM164 to rhTRAIL in vitro.
Figure 3B:
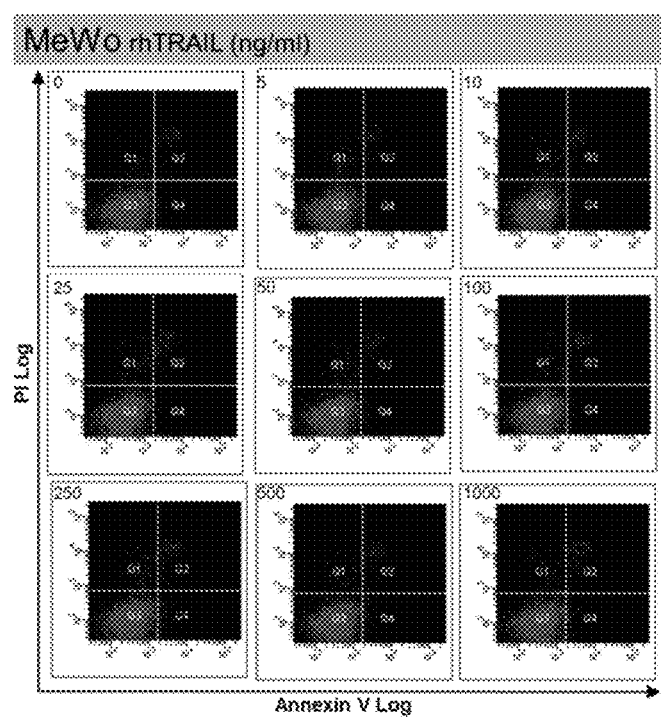
FIG. 3B shows a representative histogram of MeWo.
Figure 3C:
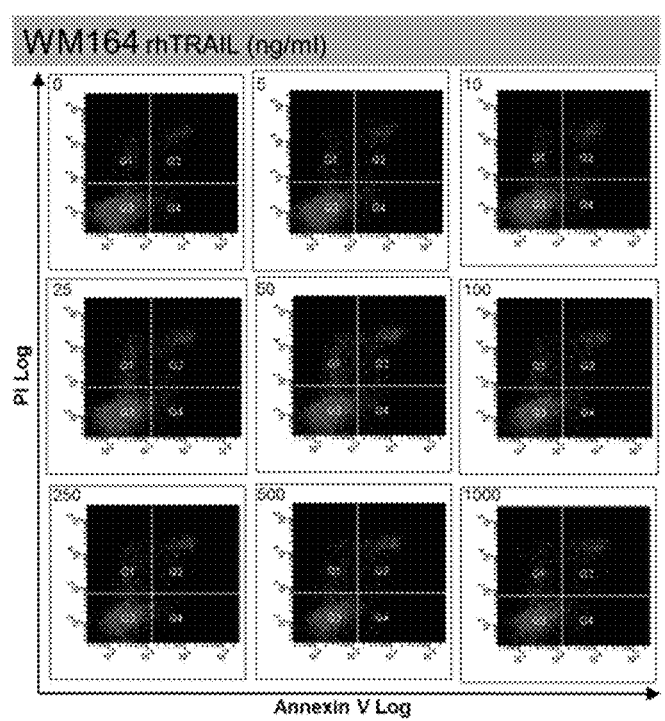
FIG. 3C shows a representative histogram of WM164.
Figure 3D:
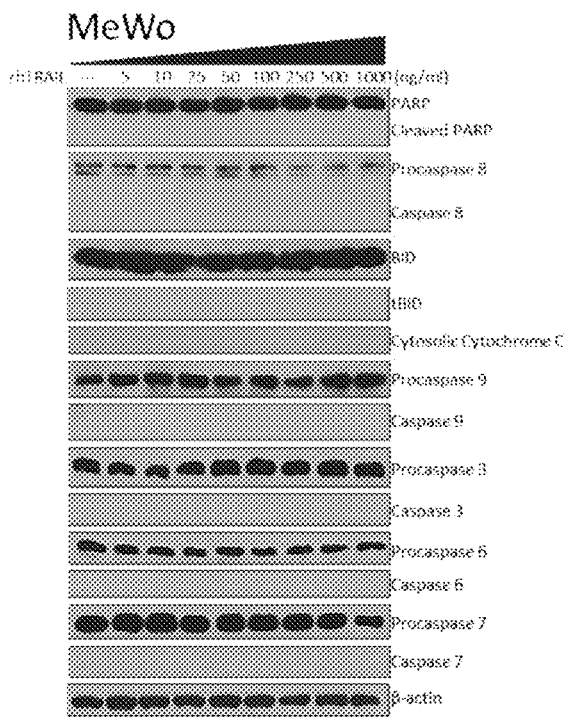
FIG. 3D shows MeWo subjected to western blot analysis and probed with anti-PARP, caspase 8, Bid, cytochrome c, caspase 9, caspase 3, caspase 6 and caspase 7.
Figure 3E:
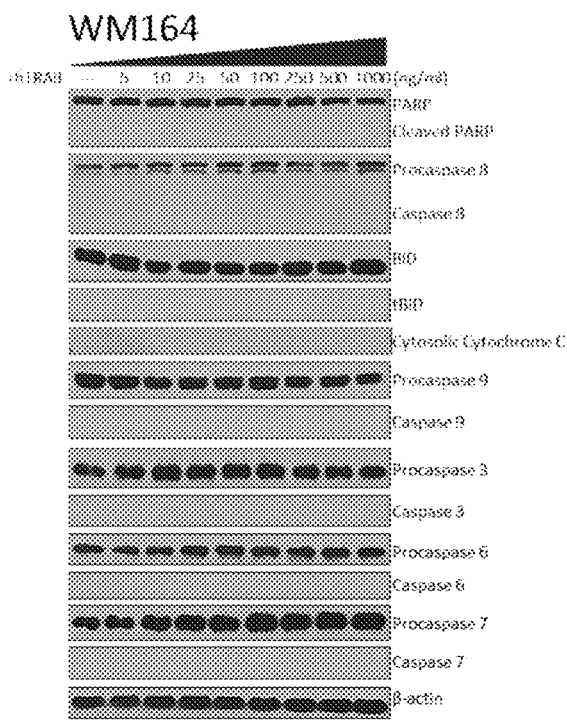
FIG. 3E shows WM164 subjected to western blot analysis and probed with anti-PARP, caspase 8, Bid, cytochrome c, caspase 9, caspase 3, caspase 6 and caspase 7.
Figure 4A:
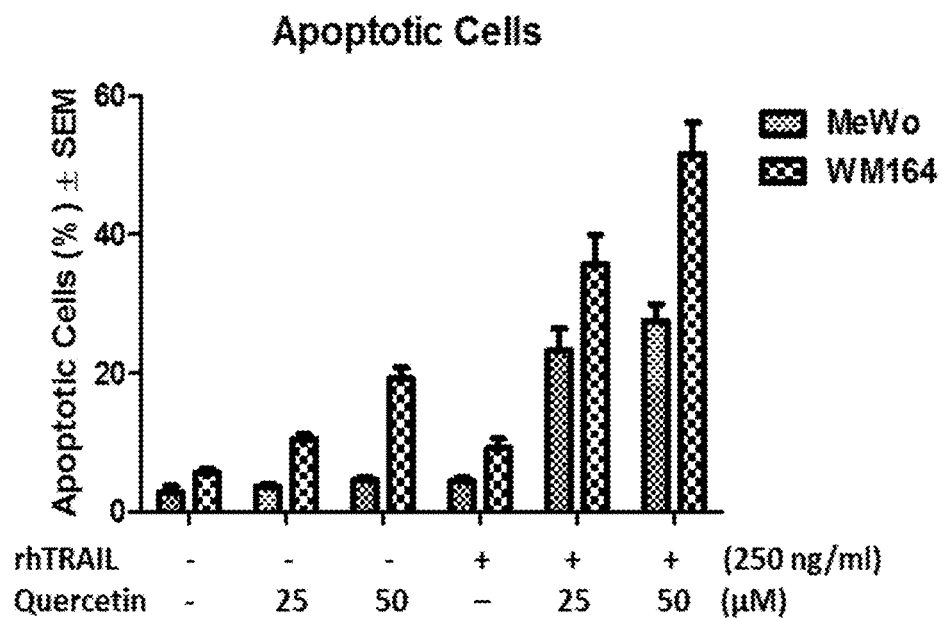
FIG. 4A shows rhTRAIL plus quercetin-induced apoptosis, including combination treatment-induced treatment (average of three independent assays±SEM).
Figure 4B:
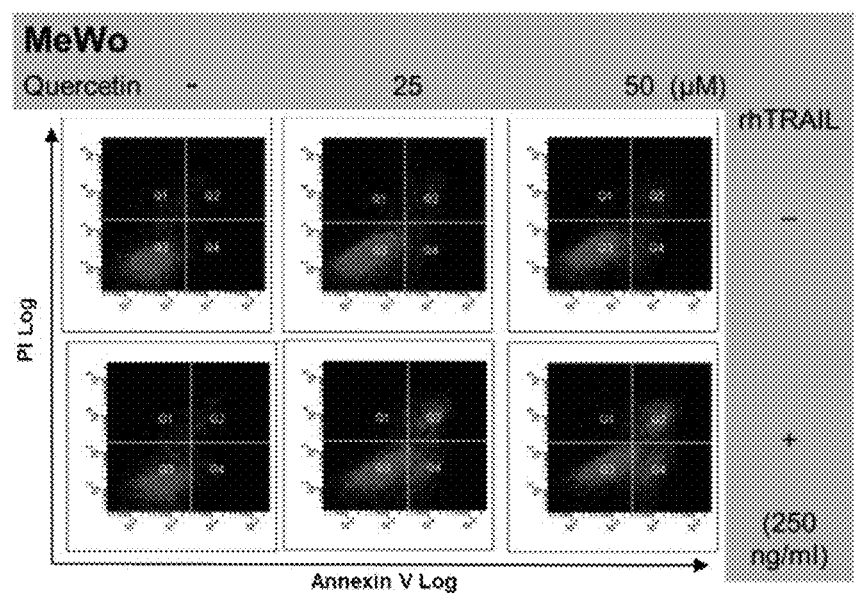
FIG. 4B shows a representative histogram of MeWo.
Figure 4C:
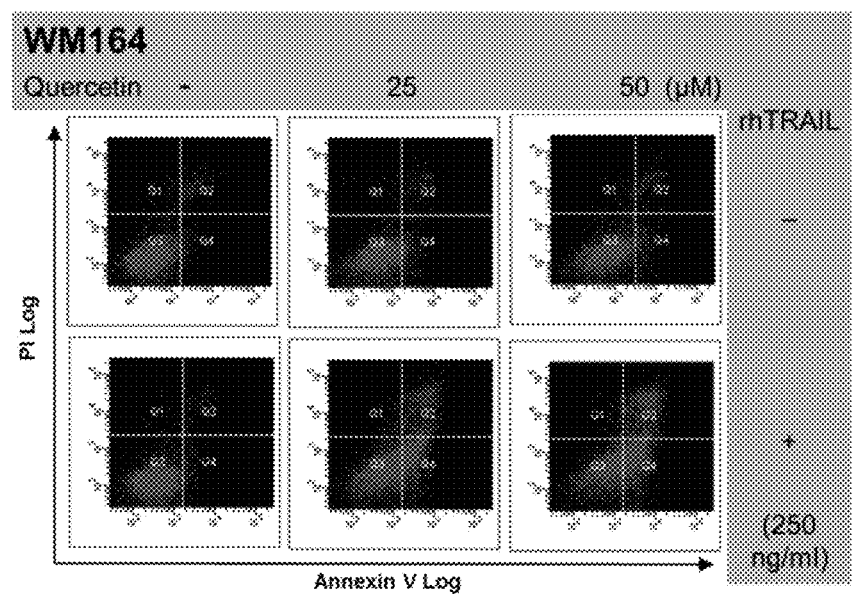
FIG. 4C shows a representative histogram of WM164.
Figure 4D:
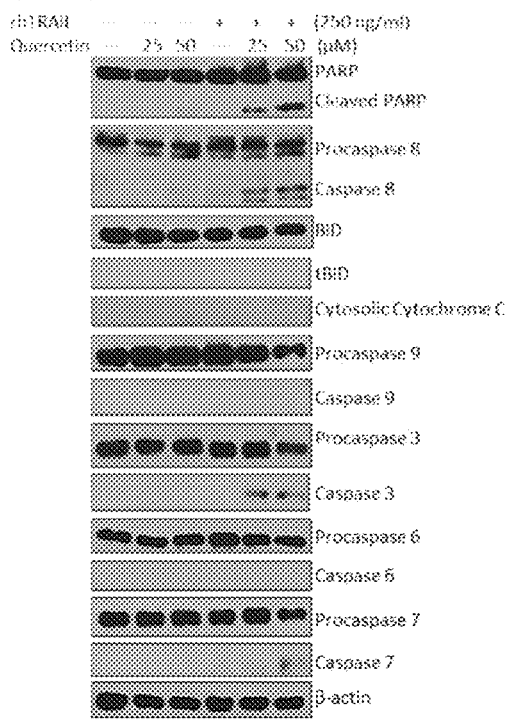
FIG. 4D shows MeWo subjected to western blot analysis and probed with anti-PARP, caspase 8, Bid, cytochrome c, caspase 9, caspase 3, caspase 6 and caspase 7.
Figure 4E:
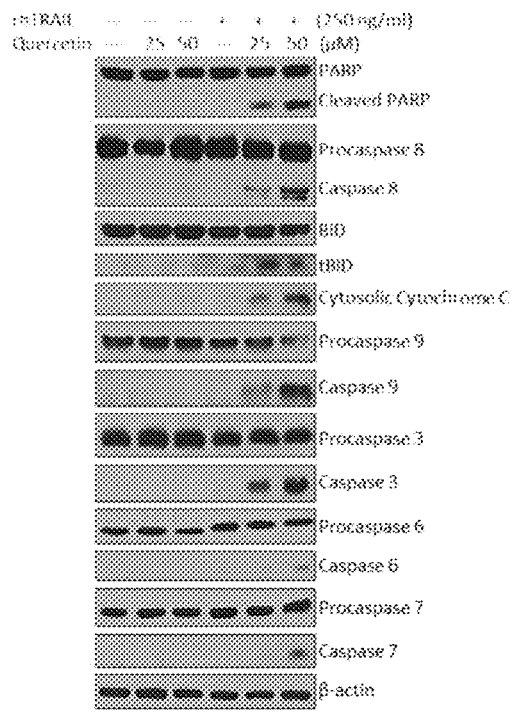
FIG. 4E shows WM164 subjected to western blot analysis and probed with anti-PARP, caspase 8, Bid, cytochrome c, caspase 9, caspase 3, caspase 6 and caspase 7.
Figure 4F:
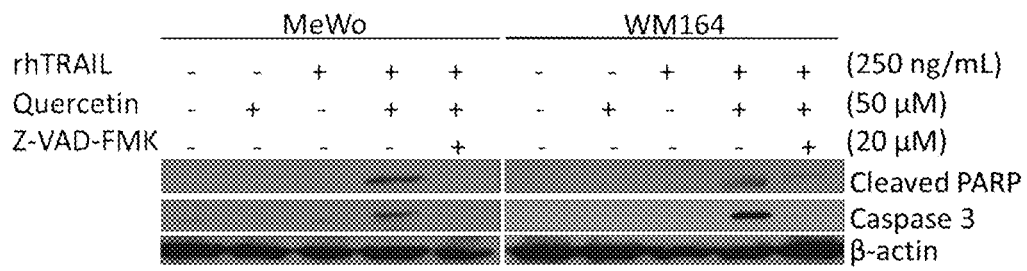
FIG. 4F shows effects of general caspase inhibitor Z-VAD-FMK on induction of apoptosis.

The rhTRAIL-resistant status of the melanoma lines were confirmed through western blotting by probing with antibodies to several key components of the apoptotic cascade (FIGS. 3D & 3E). The lack Poly (ADP-ribose) Polymerase (PARP) cleavage or activation of any proteins in the apoptotic pathway confirmed the rhTRAIL-resistance of both lines.

rhTRAIL plus quercetin apoptosis: To overcome the intrinsic rhTRAIL-resistance of MeWo and WM164, the combination treatment of rhTRAIL plus quercetin was employed. Melanoma lines were treated with single agent rhTRAIL at 250 ng/ml, quercetin at 25 and 50 μM and with the combination of the single agents.

FIG. 4 shows rhTRAIL plus quercetin-induced apoptosis. Combination treatment-induced apoptosis. FIG. 4A: Average of three independent assays±SEM. FIG. 4B: Representative histogram of MeWo. FIG. 4C: Representative histogram of WM164. Lower left quadrant: Viable cells (Annexin$^-$/PI$^-$), Lower right quadrant: Early apoptotic cells (Annexin$^+$/PI$^-$), Upper right quadrant: Late apoptotic cells (Annexin$^+$/PI$^+$). FIGS. 4D MeWo and 4E WM164±rhTRAIL subjected to western blot analysis and probed with anti-PARP, caspase 8, Bid, cytochrome c, caspase 9, caspase 3, caspase 6 and caspase 7. f3-actin was used as a loading control for each membrane. Representative f3-actin is depicted. 4F: Effects of general caspase inhibitor Z-VAD-FMK on induction of apoptosis.

Post treatment cells were collected and analyzed for induction of apoptosis through Annexin-V and PI staining and western blotting probing for key proteins in the apoptotic pathways (FIG. 4). Alone, quercetin induced minimal levels of apoptosis in the rhTRAIL-resistant melanoma cells. For MeWo there was no significant induction of apoptosis when treating with both concentrations of quercetin marked by the lack of Annexin-V$^+$ and/or Annexin-V$^+$ and PI$^+$ cells as compared to the control (P>0.05) (FIGS. 4A & 4B). The lack of quercetin-induced apoptosis was confirmed by western blot where there was no PARP cleavage or activation of any pro-apoptotic proteins (FIG. 4D). However, in WM164, quercetin was able to induce minimal levels of apoptosis with the formation of 10.5±0.7% apoptotic cells at 25 μM and 19.1±1.6% apoptotic cells at 50 μM (P<0.05) (FIGS. 4A & 4C). Probing for apoptotic proteins did not reveal any PARP cleavage or protein activation the in quercetin-treated WM164 cells as the low levels of apoptosis was not sufficient to be detected by western blotting (FIG. 4E). Furthermore, by combining rhTRAIL plus quercetin the minimal levels of apoptosis induced in the single agent treatments were dramatically increased in both melanoma lines. This was evidenced by the significantly higher formation of Annexin-V$^+$ and/or Annexin-V$^+$ and PI$^+$ cells as compared to any single agent treatments (P<0.05) (FIG. 4 A-C). The augmentation of apoptosis occurred dose-dependently in respect to quercetin. The ability of quercetin to sensitize rhTRAIL-resistant melanomas to undergo apoptosis was confirmed by western blotting (FIGS. 4 D&E). In both melanoma lines, PARP was cleaved in only the co-treatment group dose-dependently. By adding quercetin to the rhTRAIL-treatment, the once resistant cells were sensitized to activate the rhTRAIL-mediated extrinsic pathway of apoptosis as marked by the cleavage of pro-caspase 8 to caspase 8. Additionally, through the co-treatment the intrinsic pathway of apoptosis was activated in WM164 but not in MeWo as noted by the cleavage of BID to tBID followed by the release of cytochrome c into the cytosol and the activation of caspase 9 from pro-caspase 9. Finally, through the co-treatment executioner caspases were activated. In both melanoma lines caspase 3 was activated through the co-treatment, caspase 6 in only the highest co-treatment in WM164 and caspase 7 in the highest co-treatment in both melanoma lines. The role of enhanced caspase activation in the sensitization of rhTRAIL-resistant malignant melanomas by quercetin was confirmed by the addition of the general caspase inhibitor Z-VAD-FMK (FIG. 4F). The inclusion of Z-VAD-FMK blocked the induction of apoptosis in the co-treatment group as indicted by the absence of PARP cleavage and activation of caspase 3.

Quercetin regulation of death receptors: The addition of quercetin to rhTRAIL was able to promote the activation of the rhTRAIL-mediated extrinsic apoptotic pathway evidenced by the activation of caspase 8 in only the co-treatment groups. To elucidate the mechanism of quercetin sensitization, the most apical part of the extrinsic apoptotic pathway, expression of rhTRAIL-binding receptors DR4 and DR5 were examined in response to quercetin-treatment (FIG. 5).

FIG. 5 shows regulation of death receptors by quercetin. Effects of quercetin on DR4 and DR5 expression. FIG. 5A: Membrane expression of DR4. Fold increase relative to control±SEM. FIG. 5B: Membrane expression of DR5. Fold increase relative to control±SEM. FIG. 5C: Total DR4 protein. FIG. 5D: Total DR5 protein. FIG. 5E: DR4 and DR5 mRNA signal. FIG. 5F: MeWo. FIG. 5G: WM164. Membrane and cytoplasmic expression of DR4. Fold increase relative to control DR4 membrane expression±SEM.

Figure 5A:
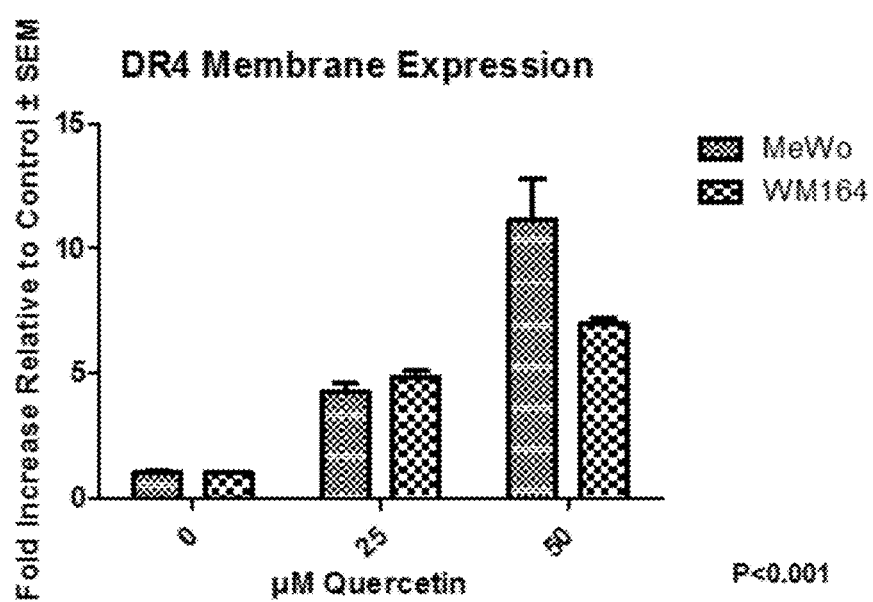
FIG. 5A shows quercetin regulation of death receptors. Effects of quercetin on DR4 and DR5 expression, including membrane expression of DR4.
Figure 5B:
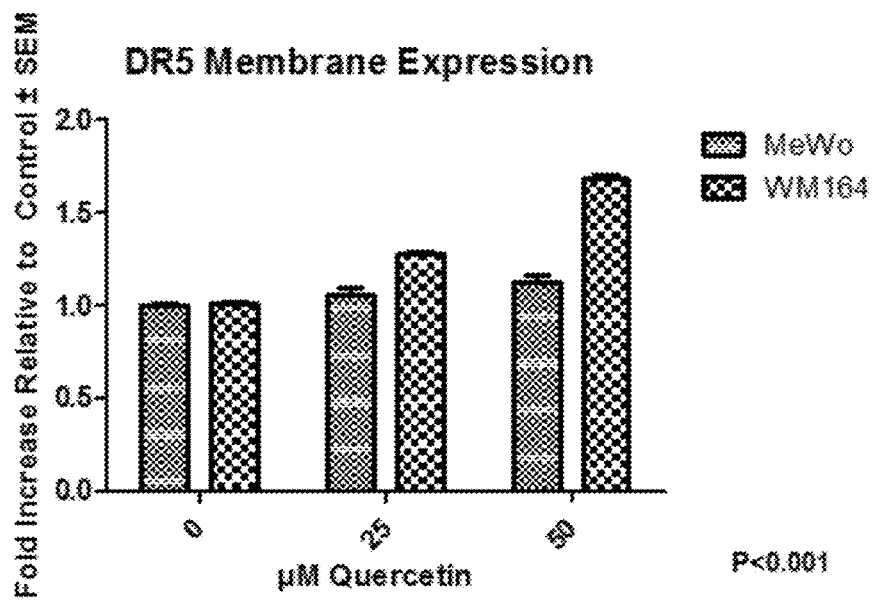
FIG. 5B shows membrane expression of DR5.
Figure 5C:
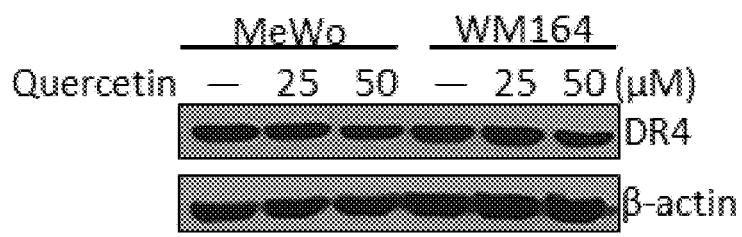
FIG. 5C shows total DR4 protein.
Figure 5D:
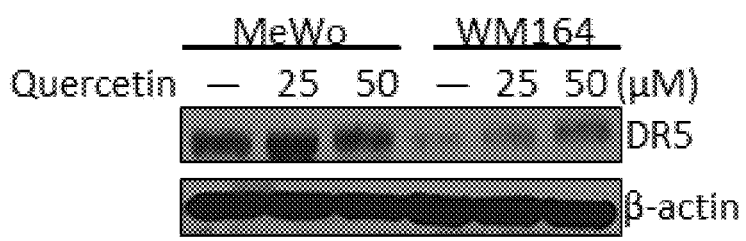
FIG. 5D shows total DR5 protein.
Figure 5E:
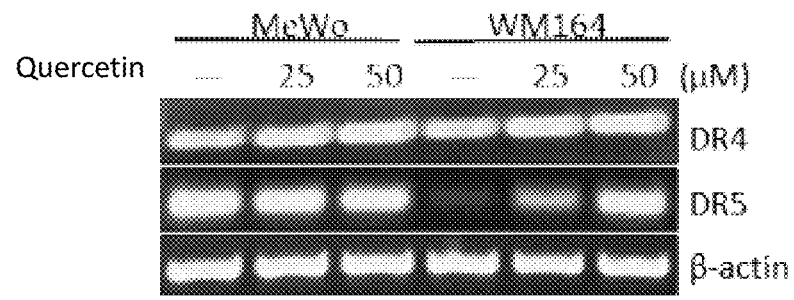
FIG. 5E shows DR4 and DR5 mRNA signal.
Figure 5F:
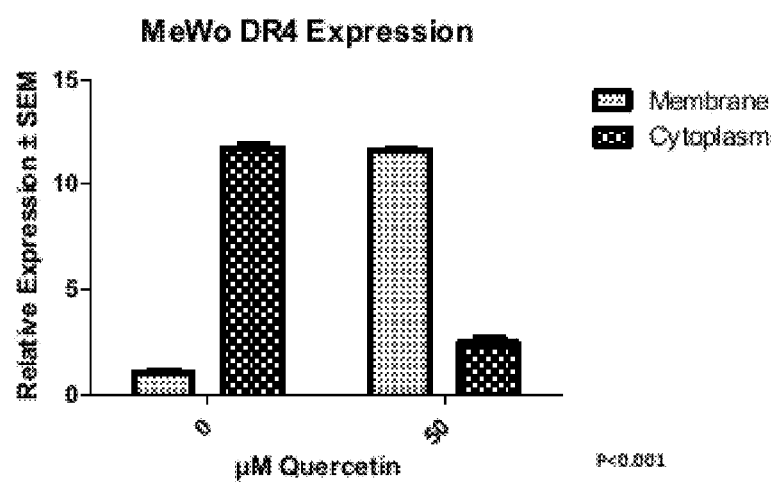
FIG. 5F shows results for MeWo.
Figure 5G:
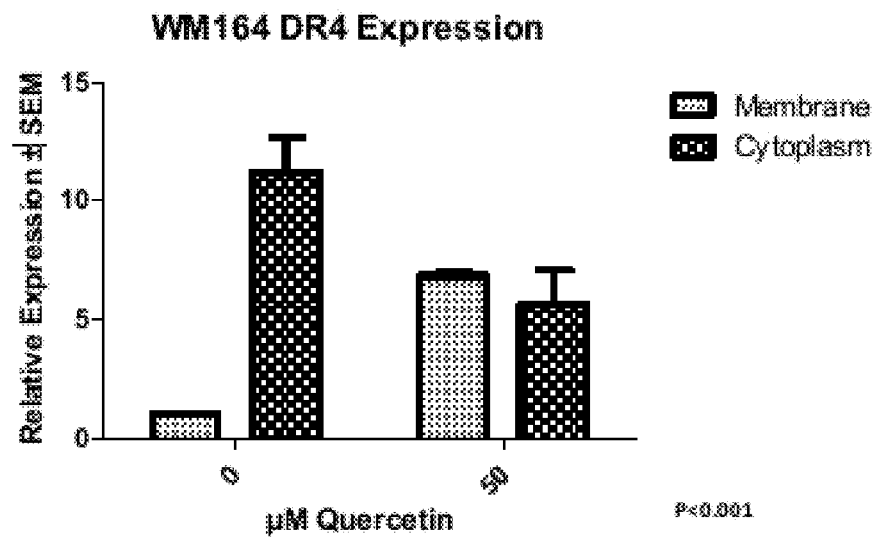
FIG. 5G shows results for WM164.

Quercetin was able to upregulate the membrane expression of DR4 in both melanoma lines dose-dependently (FIG. 5A). In response to quercetin-treatment, MeWo upregulated DR4 on the cell membrane over four-fold at 25 μM and over 11-fold at 50 μM (P<0.001). For WM164, DR4 was upregulated nearly five-fold and seven-fold at 25 μM and 50 respectively (P<0.001). For DR5, the membrane expression was only upregulated in melanoma line WM164 dose-dependently with a quarter-fold increase at 25 μM and a half-fold increase at 50 μM (P<0.001) (FIG. 5B). However, this did not occur in MeWo cells (P>0.05). To further examine the effects of quercetin on the regulation of DR4 and DR5 the total protein expression and mRNA levels were analyzed post-treatment with quercetin (FIG. 5 C-E). For DR4 there was no change in the total protein expression or the mRNA message in both melanoma lines. For DR5, there was no change in the total protein expression or the mRNA in MeWo. However, there was a dose-dependent upregulation of the total DR5 protein and DR5 mRNA in WM164. To explain the increase in the membrane expression of DR4 but the lack of increase in total protein and mRNA in response to quercetin-treatment, the cytoplasmic levels of DR4 were measured (FIGS. 5F & 5G). In both melanoma lines there was significant levels of DR4 within the cytoplasm. However, with the application of quercetin the cytoplasmic levels of DR4 decreased while the membrane levels increased (P<0.001).

Quercetin regulation of FLIP: Also a player in the most apical part of the extrinsic apoptotic pathway, FLIP expression is a major regulatory point for rhTRAIL-sensitivity.

Figure 6A:
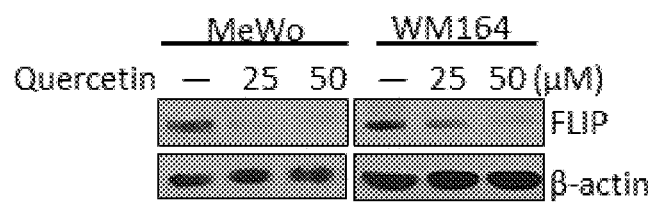
FIG. 6A shows the effects of quercetin on FLIP expression, total FLIP protein.
Figure 6B:
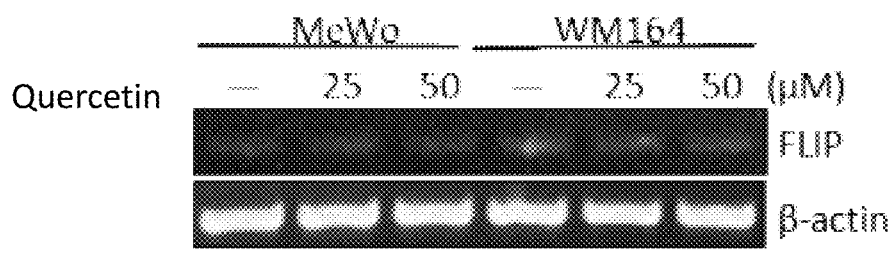
FIG. 6B shows FLIP mRNA signal.
Figure 6C:
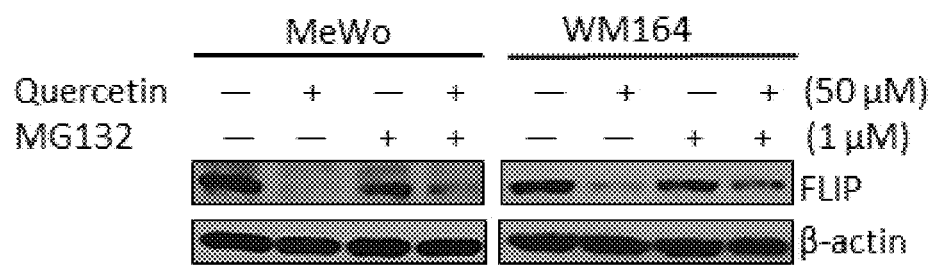
FIG. 6C shows quercetin plus proteasome inhibitor MG132 on total FLIP protein.

FIG. 6 shows quercetin regulation of FLIP, including expression. FIG. 6A: Total FLIP protein. FIG. 6B: FLIP mRNA signal. FIG. 6C: Quercetin plus proteasome inhibitor MG132 on total FLIP protein.

Quercetin was able to dose-dependently downregulate the protein expression of FLIP in both melanoma lines (FIG. 6A). To see if quercetin transcriptional downregulates FLIP, the mRNA signal of FLIP in response to quercetin-treatment was measured (FIG. 6B). Here, no change was found in the transcript signal in both lines. Another mechanism of protein downregulation is mediated through proteasomal degradation. To test if quercetin promotes the downregulation of FLIP mediated through the proteasome, the proteasome inhibitor MG132 was employed (FIG. 6C). By co-treating with quercetin and MG123, the downregulation of FLIP was prevented and it was shown that quercetin downregulates FLIP by promoting its proteasomal degradation.

Unless otherwise indicated herein, all sub-embodiments and optional embodiments are respective sub-embodiments and optional embodiments to all embodiments described herein. While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative compositions and illustrative examples shown and described. Accordingly, departures may be made from such details without departing from the spirit or scope of the applicant's general disclosure herein.

What is claimed is:

1. A method of evaluating cells from an individual to determine if a cell is sensitive to human Tumor Necrosis Factor-Related Apoptosis-Inducing Ligand (rhTRAIL) therapy, the method comprising:
   obtaining a cell sample from the individual;
   determining a level of at least one pro-apoptotic death receptor (DR) selected from DR4, DR5, and combinations thereof, expressed in a membrane of the cell;
   evaluating the cell for sensitivity to rhTRAIL therapy based on the determined level of the at least one pro-apoptotic death receptor by comparing the membrane expression level of one or more DRs to a reference standard; and
   administering a pro-apoptotic death receptor sensitizing agent if the determined level of the at least one pro-apoptotic death receptor does not exceed 1.5-fold to 6-fold the level of the reference standard.

2. The method of claim 1 wherein the DR is DR4.

3. The method of claim 1 wherein the DR is DR5.

4. The method of claim 1, wherein the level is determined by flow cytometry.

5. The method of claim 1 wherein the pro-apoptotic death receptor sensitizing agent is a polyphenol.

6. The method of claim 5, wherein the polyphenol is a naturally occurring polyphenol.

7. The method of claim 6, wherein the polyphenol is quercetin.

8. A method of evaluating cells from an individual to determine if a cell is sensitive to human Tumor Necrosis Factor-Related Apoptosis-Inducing Ligand (rhTRAIL) therapy, the method comprising:
   identifying an individual in need of rhTRAIL therapy;
   obtaining a cell sample from the individual;
   determining a membrane expression level of at least one of DR4 and DR5;
   evaluating the cell for sensitivity to rhTRAIL therapy based on the determined membrane expression level by comparing the determined membrane expression level to a reference standard; and
   administering a therapeutic amount of quercetin if the determined membrane expression level is less than 1.5-fold to 6-fold the level of the reference standard.

9. A method of treating cells via human Tumor Necrosis Factor-Related Apoptosis-Inducing Ligand (rhTRAIL) therapy, the method comprising:
   identifying an individual in need of rhTRAIL therapy;
   obtaining a cell sample from the individual;
   determining a membrane expression level of at least one of DR4 and DR5;
   evaluating the cell for sensitivity to rhTRAIL therapy based on the determined membrane expression level by comparing the determined membrane expression level to a reference standard; and
   administering a therapeutic amount of a pro-apoptotic death receptor sensitizing agent if the determined membrane expression level is less than 1.5-fold to 6-fold the level of the reference standard.

10. The method of claim 9, wherein the pro-apoptotic death receptor sensitizing agent is a polyphenol.

11. The method of claim 10, wherein the polyphenol is a naturally occurring polyphenol.

12. The method of claim 11, wherein the polyphenol is quercetin.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial sequence
<220> FEATURE:
<223> OTHER INFORMATION: synthetic

<400> SEQUENCE: 1
gggagccgct catgaggaag ttgg                                       24

<210> SEQ ID NO 2
<211> LENGTH: 24
<212> TYPE: DNA
<213> ORGANISM: Artificial sequence
<220> FEATURE:
<223> OTHER INFORMATION: synthetic

<400> SEQUENCE: 2
ggcaagtctc tctcccagcg tctc                                       24

<210> SEQ ID NO 3
<211> LENGTH: 18
<212> TYPE: DNA
<213> ORGANISM: Artificial sequence
<220> FEATURE:
<223> OTHER INFORMATION: synthetic

<400> SEQUENCE: 3
gagcaacgca gactcgct                                              18

<210> SEQ ID NO 4
<211> LENGTH: 18
<212> TYPE: DNA
<213> ORGANISM: Artificial sequence
<220> FEATURE:
<223> OTHER INFORMATION: synthetic

<400> SEQUENCE: 4
tcactccaag gacacggc                                              18

<210> SEQ ID NO 5
<211> LENGTH: 20
<212> TYPE: DNA
<213> ORGANISM: Artificial sequence
<220> FEATURE:
<223> OTHER INFORMATION: synthetic

<400> SEQUENCE: 5
cttggccaat ttgcctgtat                                            20

<210> SEQ ID NO 6
<211> LENGTH: 20
<212> TYPE: DNA
<213> ORGANISM: Artificial sequence
<220> FEATURE:
<223> OTHER INFORMATION: synthetic

<400> SEQUENCE: 6
cccatgaaca tcctcctgat                                            20

<210> SEQ ID NO 7
<211> LENGTH: 24
<212> TYPE: DNA
<213> ORGANISM: Artificial sequence

```
<220> FEATURE:
<223> OTHER INFORMATION: synthetic

<400> SEQUENCE: 7
tgacggggtc acccacactg tgcc                                          24

<210> SEQ ID NO 8
<211> LENGTH: 23
<212> TYPE: DNA
<213> ORGANISM: Artificial sequence
<220> FEATURE:
<223> OTHER INFORMATION: synthetic

<400> SEQUENCE: 8
ctgcatcctg tcggcaatgc cag                                           23
```